United States Patent [19]

Babler

[11] Patent Number: 5,952,519
[45] Date of Patent: Sep. 14, 1999

[54] C-15 PHOSPHONATE REAGENT COMPOSITIONS FOR THE MANUFACTURE OF COMPOUNDS SUCH AS CANTHAXANTHIN AND METHODS OF SYNTHESIZING THE SAME

[75] Inventor: James H. Babler, Chicago, Ill.

[73] Assignee: Loyola University of Chicago, Chicago, Ill.

[21] Appl. No.: 09/220,858

[22] Filed: Dec. 28, 1998

[51] Int. Cl.[6] ............................... C07F 9/40; C07C 49/653
[52] U.S. Cl. ........................... 558/198; 558/87; 568/363; 568/367
[58] Field of Search ............................. 558/198; 568/367

[56] References Cited

U.S. PATENT DOCUMENTS

| 3,197,497 | 7/1965 | Olivette . | |
|---|---|---|---|
| 4,000,198 | 12/1976 | Rosenberger . | |
| 5,061,819 | 10/1991 | Babler | 558/87 |
| 5,847,185 | 12/1998 | Babler | 558/83 |

OTHER PUBLICATIONS

*Chemical Abstracts* 1965, 63, 13318e of U.S. Patent No. 3,197,497.
*Chemical Abstracts* 1972, 76, 4035g of German Patent No. 2,109,875.
*Chemical Abstracts* 1977, 86, 155834z of German Patent No. 2,534,805.
*Chemical Abstracts* 1977, 87, 39706f of U.S. Patent No. 4,000,198.
*Chemical Abstracts* 1981, 94, 174463j of European Patent Application 17,800.
*Chemical Abstracts* 1982, 96, 199941t of Japanese Patent 81,161,370.
Entschel, et al., *Helv. Chim. Acta.* 1958, 41, 402–413.
Becher, et al., *Helv. Chim. Acta.* 1981, 64, 2419–2435.
Hibbert, et al., *J. Am. Chem Soc.* 1924, 46, 119–130.
Michalski, et al., *J. Chem. Soc.* 1961, 4904–4906.
Rosenberger, et al., *J. Org. Chem.* 1982, 47, 2130–2134.
Brooks, et al., *J. Org. Chem.* 1983, 48, 277–278.
Brooks, et al., *J. Org. Chem.* 1985, 50, 628–632.
Ranu, et al., *J. Org. Chem.* 1988, 63, 5250–5251.
Johnson, et al., *Org. Synth.*, 1950, 30, 18–21.
Rosenberger, et al., *Pure & Appl. Chem.,* 1979, 51, 871–886.
Bernhard, et al., *Pure & Appl. Chem.,* 1991, 63, 35–44.
Bertram, *Pure & Appl. Chem.,* 1994, 66, 1025–1032.
Mal'kina, et al., *Synthesis,* 1996, 589–590.
Altenbach, et al., *Tetrahedron Letters,* 1981, 22, 5175–5178.
Ohtuska, et al., *Tetrahedron Letters,* 1986, 27, 203–206.
Ranu, et al., *Tetrahedron Letters,* 1994, 35, 8649–8650.
Swindell, et al., *Tetrahedron Letters,* 1994, 35, 4959–4962.

*Primary Examiner*—Michael G. Ambrose
*Attorney, Agent, or Firm*—Marshall, O'Toole, Gerstein, Murray & Borun

[57] ABSTRACT

The present invention describes novel C-15 allenic phosphonate reagent compositions of the formula:

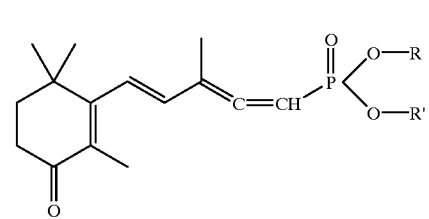

(8)

R and R' = $C_1$–$C_4$ alkyl groups or R, R' = $(CH_2)_n$ ($n$ = 2 or 3)

The invention also describes novel C-15 allylic phosphonate reagent compositions of the formula:

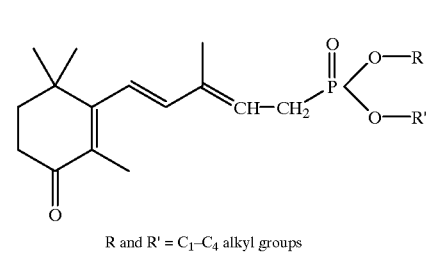

(9)

R and R' = $C_1$–$C_4$ alkyl groups

The invention also describes methods of preparing canthaxanthin, the phosphonate reagent compositions, and a tertiary propargylic alcohol of the formula:

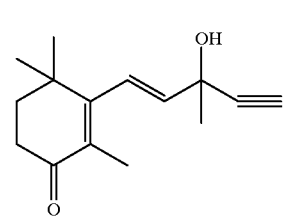

(7)

29 Claims, No Drawings

C-15 PHOSPHONATE REAGENT COMPOSITIONS FOR THE MANUFACTURE OF COMPOUNDS SUCH AS CANTHAXANTHIN AND METHODS OF SYNTHESIZING THE SAME

BACKGROUND OF THE INVENTION

1. Field of the Invention

The present invention describes novel phosphonate reagent compositions of the formula:

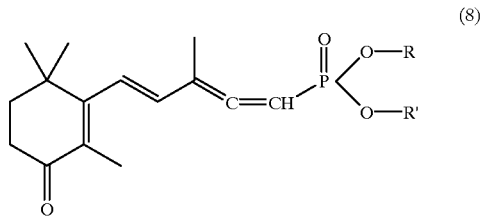

(8)

wherein R and R'=$C_1$–$C_4$ alkyl groups or R, R'=$(CH_2)_n$ (n=2 or 3).

Allenic phosphonate reagent compositions (8) can be partially reduced to form allylic C-15 phosphonate compounds of the formula:

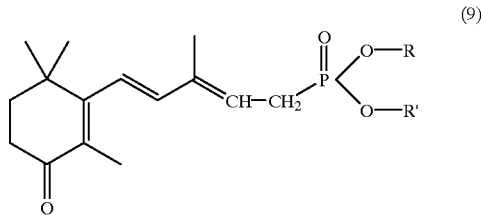

(9)

wherein R and R'=$C_1$–$C_4$ alkyl groups.

Also described are methods of preparing a tertiary propargylic alcohol of the formula:

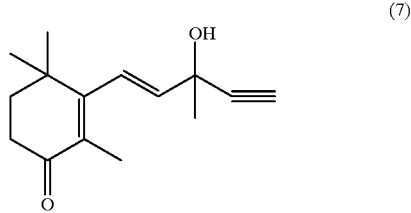

(7)

(systematically named 3-(3-hydroxy-3-methylpent-1-en-4-ynyl)-2,4,4-trimethylcyclohex-2-en-1-one), which can be used to prepare the phosphonate compositions (8) and (9).

2. Description of Related Art (a) Utility and Preparation of Canthaxanthin

Of the approximately 600 naturally occurring carotenoids, only six are produced commercially. Although β-carotene is the carotenoid with the strongest sales, during the past two decades production of astaxanthin (used in the "fish-farming" industry) and canthaxanthin (11) has rapidly increased. Canthaxanthin (11), which has been used in the poultry industry for several decades, was initially manufactured using a process that started with β-carotene. [Reference: R. Entschel and P. Karrer, *Hely. Chim. Acta* 1958, 41 402]. However, this type of approach to canthaxanthin is unattractive for several reasons: (a) the high cost of β-carotene; (b) the large volume of solvents that are required when conducting reactions involving C-40 compounds; and, most importantly, the yield of canthaxanthin (based on the β-carotene that is consumed) is moderate (50–65%) at best. For specific examples of this oxidative process, see German patent 2,534,805 (Feb. 10, 1977, issued to BASF) [*Chem. Abstracts* 1977, 86, 155834z] and German patent 2,109,875 (Sep. 30, 1971, issued to Rhone-Poulenc) [*Chem. Abstracts* 1972, 76, 4035g].

By the early 1980's, the demand for canthaxanthin began to grow when various coaltar-based azo dyes were removed from the certified list of dyes permitted for use in foods and drugs. Canthaxanthin, which exhibits excellent tinctorial properties, was able to satisfy the need for a safe red coloring agent for human use.

An additional factor that could increase the market for canthaxanthin is its role in the chemoprevention of cancer. Recent studies in both mouse and human cells indicate that canthaxanthin can function in the post-initiation phase of carcinogenesis by suppressing the ability of carcinogen-initiated cells to undergo neoplastic transformation. [Reference: J. S. Bertram, *Pure & Appl. Chem.*, 1994, 66, 1025].

In order to meet the demand for increased production of canthaxanthin, several convergent syntheses (i.e., routes involving the coupling of smaller fragments, each of which was synthesized independently) were developed. Among these routes, the most noteworthy one was developed at Hoffmann-La Roche. [References: M. Rosenberger, et al., *J. Org. Chem.* 1982, 47, 2130; U.S. Pat. No. 4,000,198 (Dec. 28, 1976), which is cited in *Chem. Abstracts* 1977, 87, 39706f, and M. Rosenberger, et al., *Pure & Appl. Chem.* 1979, 51, 871]. The latter route involves a Wittig coupling of a C-15 phosphonium salt and the symmetrical C-10 dialdehyde (10) (2,7-dimethyl-2,4,6-octatrienedial) to generate canthaxanthin. Although employing straightforward chemical operations, this approach suffers from the use of a costly raw material (triphenylphosphine) as well as too many steps (approximately 13 reactions are required to construct the C-15 phosphonium salt). Researchers at Hoffmann-La Roche [K. Bernhard and H. Mayer, *Pure & Appl. Chem.* 1991, 63, 35] have recently indicated that this last step is a problem for the manufacture of canthaxanthin and related polyenes: "A major drawback of this olefination reaction, however, is the formation of triphenylphosphine oxide which, on an industrial production scale, has to be recycled by reduction to triphenylphosphine. Any type of synthesis which circumvents problems of that kind is of potential value in large scale synthesis of polyenes."

Another route to canthaxanthin involves a ten-step process starting with α-ionone (3) and the symmetrical dialdehyde 10. [Reference: K. Bernhard and H. Mayer, *Pure & Appl. Chem.* 1991, 63, 35]. A major disadvantage to this route is the fact that two chemical transformations have to be conducted after the C-40 skeleton of canthaxanthin has been obtained by coupling a C-15 sulfone intermediate to the C-10 dialdehyde 10. Difficulties associated with performing chemical transformations at the $C_{40}$ level include solubility problems and the intrinsic instability of polyene compounds.

(b) Preparation of Tertiary Propargylic Alcohol

A tertiary propargylic alcohol of the following formula:

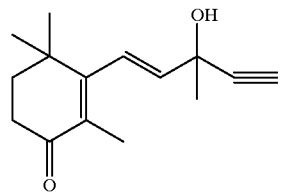

(7)

can be used to prepare the novel C-15 allenic phosphonate reagent compositions (8) and C-15 allylic phosphonate compounds (9). Tertiary propargylic alcohol (7) can be prepared in four steps from α-ionone (3), according to the following reaction sequence:

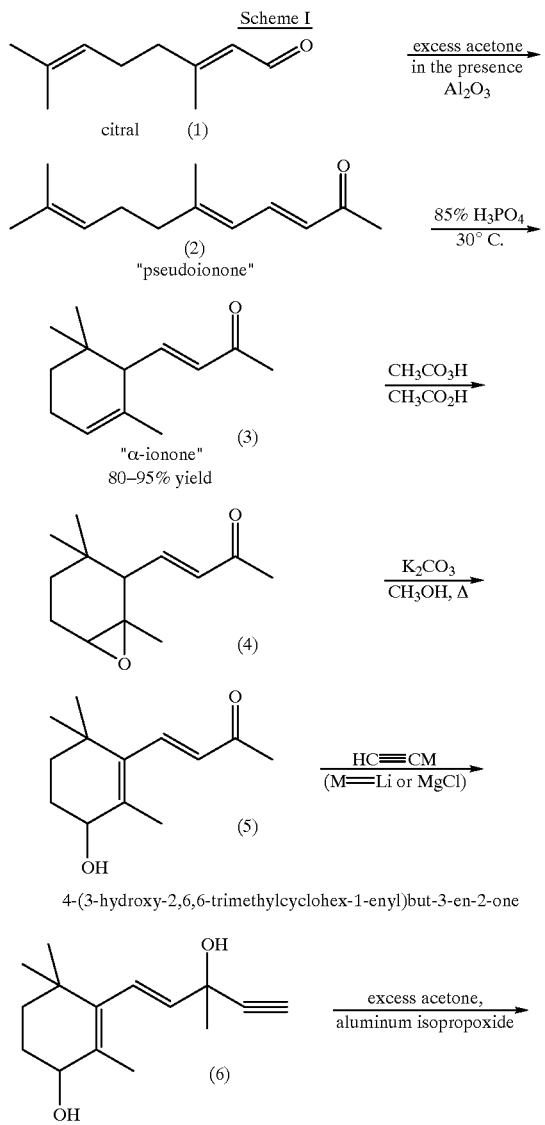

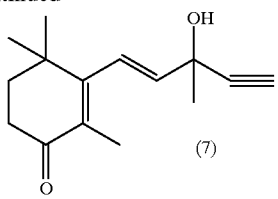

(7)

Alternatively, tertiary propargylic alcohol (7) can be prepared in three steps from β-ionone (12), according to the following reaction sequence:

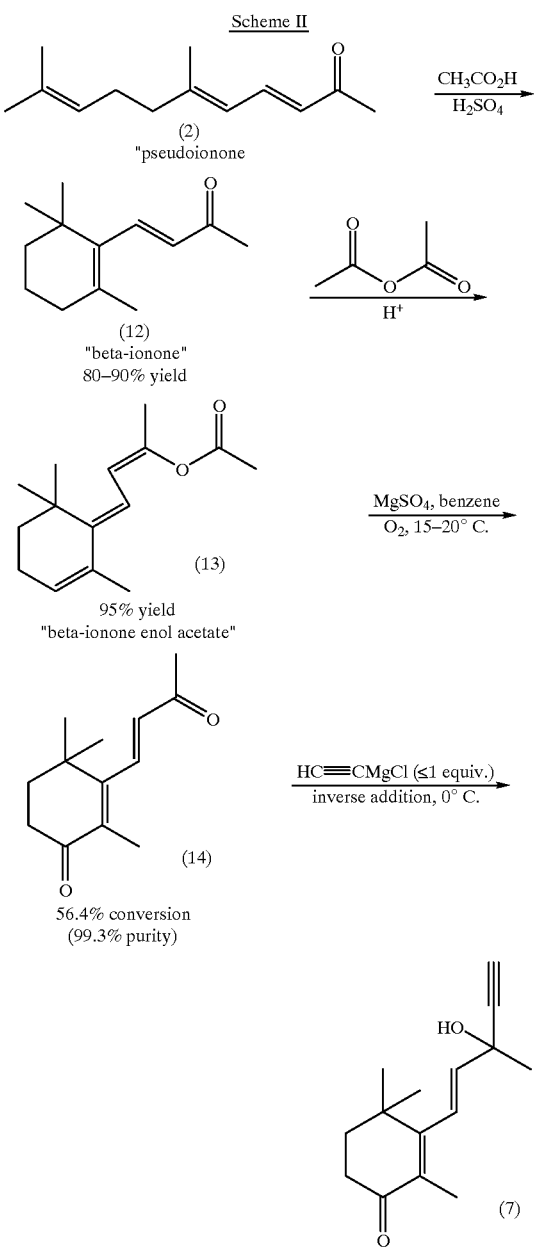

Reference for the conversion of (12) to (14):
Japanese patent 81,161,370 (Dec. 11, 1981); *Chem. Abstracts* 1982, 96, 199941t.

Both α-ionone (3) (used in Scheme I) and β-ionone (12) (used in Scheme II) are obtained in high yield in two-step processes that start with citral (1). [Reference: H. Hibbert and L. T. Cannon, *J. Am. Chem Soc.* 1924, 46, 119]. It should be noted that all of the above-described transformations for preparing tertiary propargylic alcohol (7) involve straightforward chemical operations and low-cost raw materials. Furthermore, most of these transformations have previously been conducted on a large scale and been shown to afford good yields of the desired products. For example, α-ionone (3) can be converted to epoxide (4) in 98% yield [D. W. Brooks and E. Kennedy, *J. Org. Chem.,* 1983, 48, 277]; and the latter epoxide has been converted in 99% yield to hydroxy ketone (5) [M. Rosenberger, et al., *J. Org. Chem.* 1982, 47, 2130]. In addition to citral (1) and acetone, the only organic raw material required to synthesize tertiary propargylic alcohol (7) is acetylene.

SUMMARY OF THE INVENTION

The present invention describes novel C-15 allenic phosphonate reagent compositions of the formula:

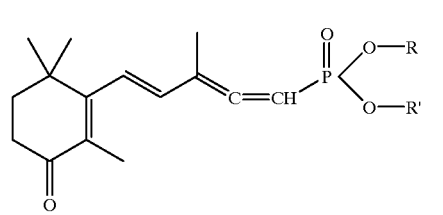

(8)

R and R' = $C_1$–$C_4$ alkyl groups or R, R' = $(CH_2)_n$ ($n$ = 2 or 3)

When R and R' are alkyl groups having up to four carbon atoms, the compounds of the present invention are systematically named as ester derivatives of an alkatrienylphosphonic acid. Thus, for example, when R=R'=ethyl, the compound is named 3-methyl-5-(2,6,6-trimethyl-3-oxocyclohex-1-enyl)-1,2,4-pentatrienylphosphonic acid, diethyl ester. Other compounds within the scope of the present invention include:

3-methyl-5-(2,6,6-trimethyl-3-oxocyclohex-1-enyl)-1,2,4-pentatrienylphosphonic acid, dimethyl ester.

3-methyl-5-(2,6,6-trimethyl-3-oxocyclohex-1-enyl)-1,2,4-pentatrienylphosphonic acid, diisopropyl ester.

3-methyl-5-(2,6,6-trimethyl-3-oxocyclohex-1-enyl)-1,2,4-pentatrienylphosphonic acid, dipropyl ester.

3-methyl-5-(2,6,6-trimethyl-3-oxocyclohex-1-enyl)-1,2,4-pentatrienylphosphonic acid, dibutyl ester.

3-methyl-5-(2,6,6-trimethyl-3-oxocyclohex-1-enyl)-1,2,4-pentatrienylphosphonic acid, diisobutyl ester.

Also within the scope of the present invention are C-15 allenic phosphonate reagents (8) in which R and R' form part of a 5- or 6-membered heterocyclic ring. Thus, for example, when R, R'=$CH_2CH_2$, the compound is named 2-[3-methyl-5-(2,6,6-trimethyl-3-oxocyclohex-1-enyl)penta-1,2,4-trienyl]-1,3,2-dioxaphospholan-2-one:

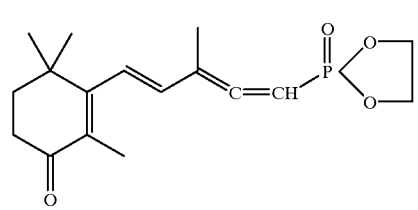

(8)

-continued

R, R' = $CH_2CH_2$

The invention also describes novel C-15 allylic phosphonates that can be represented by the formula shown below:

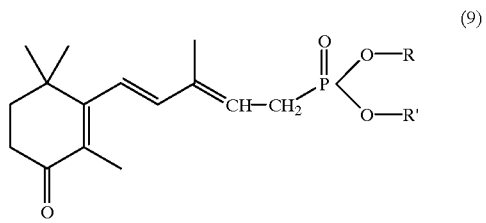

(9)

R and R' = $C_1$–$C_4$ alkyl groups

Such compounds are named as ester derivatives of an alkadienylphosphonic acid. Thus, for example, when R=R'=ethyl, the compound is named 3-methyl-5-(2,6,6-trimethyl-3-oxocyclohex-1-enyl)-2,4-pentadienylphosphonic acid, diethyl ester. Other compounds within the scope of the present invention include:

3-methyl-5-(2,6,6-trimethyl-3-oxocyclohex-1-enyl)-2,4-pentadienylphosphonic acid, dimethyl ester.

3-methyl-5-(2,6,6-trimethyl-3-oxocyclohex-1-enyl)-2,4-pentadienylphosphonic acid, diisopropyl ester.

3-methyl-5-(2,6,6-trimethyl-3-oxocyclohex-1-enyl)-2,4-pentadienylphosphonic acid, dipropyl ester.

3-methyl-5-(2,6,6-trimethyl-3-oxocyclohex-1-enyl)-2,4-pentadienylphosphonic acid, dibutyl ester.

3-methyl-5-(2,6,6-trimethyl-3-oxocyclohex-1-enyl)-2,4-pentadienylphosphonic acid, diisobutyl ester.

The invention also relates to a method for preparing tertiary propargylic alcohol (7), which is summarized by the following reaction sequence:

Scheme III (a)

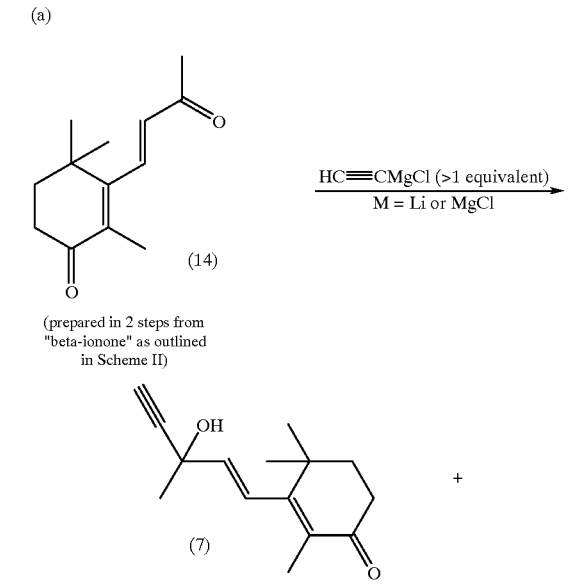

-continued

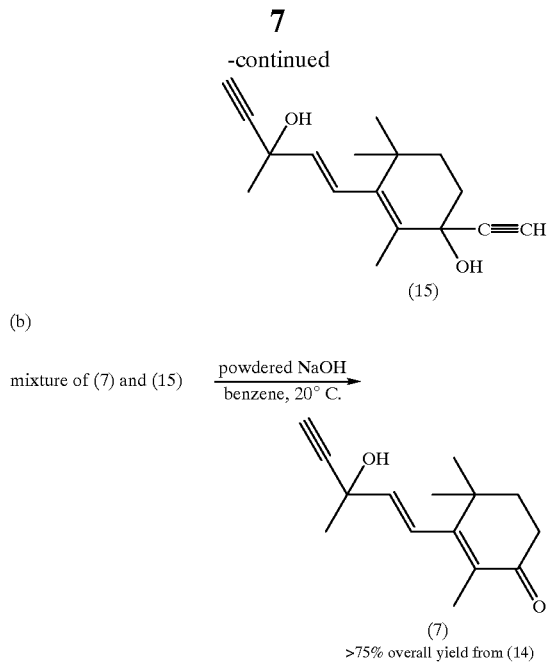

(b) mixture of (7) and (15) →powdered NaOH/benzene, 20° C.→ (7) >75% overall yield from (14)

This selective "retro-alkynylation" of diyne-diol (15) produces alkynol (7), the direct precursor to allenic phosphonate (8). This type of transformation (i.e., collapse of a tertiary alkynol to yield a carbonyl compound) has precedent in the literature: A. G. Mal'kina, et al., *Synthesis* 1996, 589 and C. S. Swindell, et al., *Tetrahedron Lett.* 1994, 35, 4959 (conversion of 9 to 10). However, the substrate (15) has two tertiary alkynol functionalities. The selective "collapse" of only one of these groups, which was observed in Scheme III, was not predictable.

The conditions used include treatment of (15) (or mixtures of (15) and (7)) with powdered NaOH (or KOH) in a nonpolar organic solvent at room temperature (or gentle heating; the reaction temperature must be lower than 75° C.). Suitable solvents include aromatic hydrocarbons (toluene, xylene, benzene), ethers (e.g., diisopropyl ether), chlorobenzene, or mixtures thereof An alternate approach to tertiary alkynol (7) that involved addition of one molar equivalent of acetylide to diketone (14) (SCHEME II) was not as successful—alkynol (7) was the major product, but it was always contaminated with the bis adduct (15) and unreacted starting diketone (14).

The invention also relates to methods of preparing C-15 allenic phosphonates (8) and C-15 allylic phosphonates (9), which are illustrated by the following reaction sequence:

Scheme IV

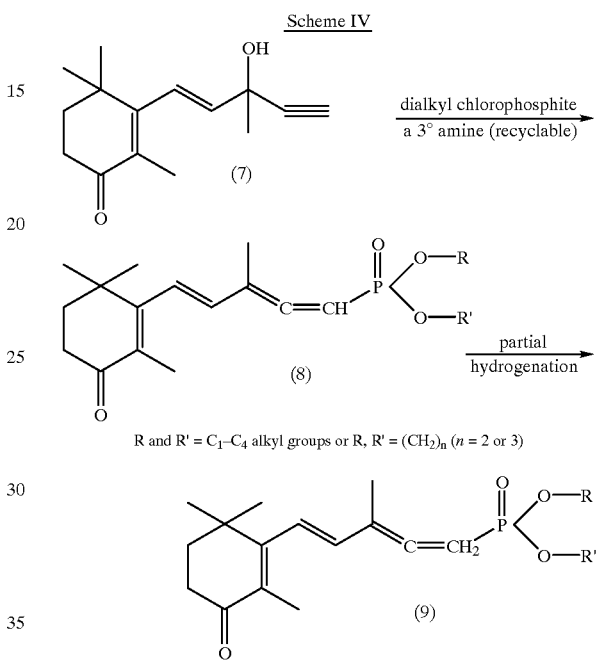

R and R' = $C_1$–$C_4$ alkyl groups or R, R' = $(CH_2)_n$ ($n$ = 2 or 3)

The invention also relates to a method for preparing canthaxanthin (11), illustrated by the following reaction sequence:

Scheme V

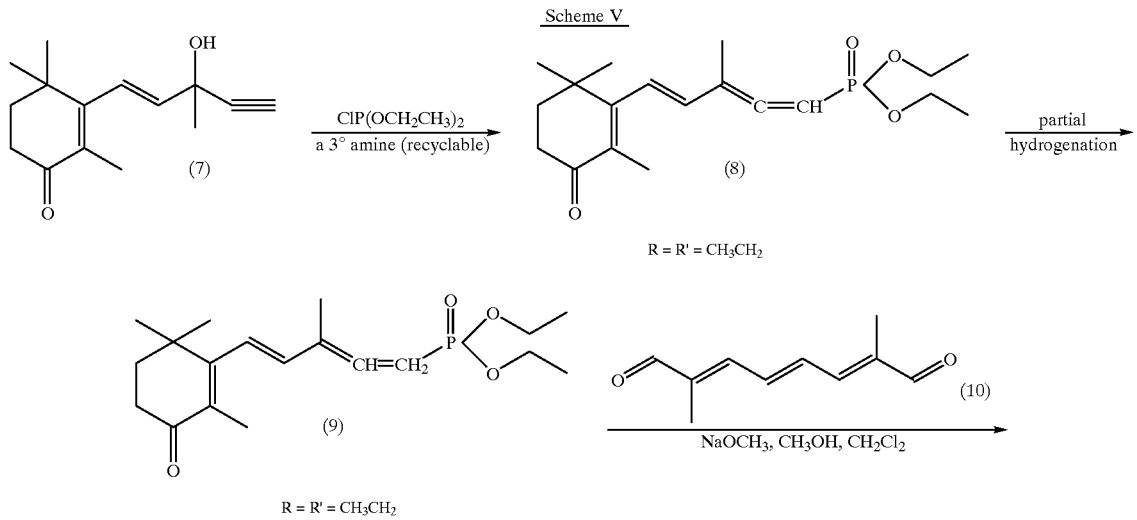

R = R' = $CH_3CH_2$

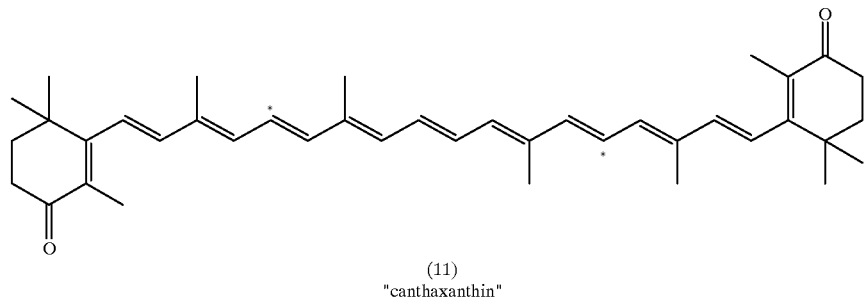

(11)
"canthaxanthin"

As shown in reaction Schemes IV and V, once alcohol (7) has been obtained, only two steps [both of which proceed in 90–100% yield and result in the formation of novel C-15 phosphonates (8) and (9)] are required to obtain the direct precursor (C-15 allylic phosphonate (9)) to canthaxanthin (11). Treatment of tertiary propargylic alcohol (7) with one equivalent of diethyl chlorophosphite [prepared by treatment of $PCl_3$ with 2 equivalents of ethyl alcohol in a nonpolar solvent as described in *J. Chem. Soc.* 1961, 4904] afforded, after spontaneous rearrangement of an initially-formed, non-isolable phosphite ester, the novel C-15 allenic phosphonate (8) in virtually quantitative yield.

This rearrangement process (i.e., conversion of (7) to (8)) is not a novel process per se. A variety of structurally-simple tertiary propargylic alcohols have been converted to allenic phosphonates in a similar type of process. [References: U.S. Pat. No. 3,197,497 (Jul. 27, 1965), which is cited in *Chem. Abstracts* 1965, 63, 13318e; and H.-J. Altenbach and R. Korff, *Tetrahedron Lett.* 1981, 22, 5175]. As reported in U.S. patent application Ser. No. 08/975,819, filed Dec. 8, 1997, the applicant has recently utilized a similar process to prepare a structurally-different C-15 allenic phosphonate that could be used to synthesize both β-carotene and vitamin A.

The penultimate step in this novel route to canthaxanthin involves the partial hydrogenation of allenic phosphonate (8). It was found that the desired transformation (i.e., conversion of (8) to (9)) could be achieved using one equivalent of ammonium formate in methyl alcohol. Alternatively, a trialkylammonium formate may be used. The reaction is catalyzed by a transition metal catalyst, such as a palladium catalyst. Similar reaction conditions have been reported [B. C. Ranu and A. Sarkar, *Tetrahedron Lett.* 1994, 35, 8649] for the selective reduction of carbon-carbon double bonds conjugated to a carbonyl group; yet the double bond reduced in the conversion of (8) to (9) is the only one that is not conjugated to the carbonyl functionality.

The synthesis of canthaxanthin is completed by the base-promoted coupling of C-15 allylic phosphonate (9) to the well-known symmetrical dialdehyde (10) [2,7-dimethyl-2,4,6-octatrienedial]. Researchers at Hoffmann-La Roche have used similar conditions to couple (10) to an analogous (but considerably more costly) C-15 phosphonium salt [M. Rosenberger, et al., *J. Org. Chem.* 1982, 47, 2130].

The disclosed methods have the following advantages:
(a) All reactions involve straightforward chemical operations and proceed in high yield.
(b) The number of chemical reactions required to convert β-ionone to C-15 allylic phosphonate (9) (the immediate precursor to canthaxanthin) is 5.
(c) No costly raw materials are used in this new route to canthaxanthin.
(d) One of the novel intermediates, phosphonate (8), could prove to be a useful precursor to the valuable carotenoid, astaxanthin—sales of which continue to grow at a rapid rate.

DETAILED DESCRIPTION OF THE INVENTION

The following examples are presented for purposes of illustration and should not be construed as limiting the invention which is delineated in the claims.

EXAMPLE I

Preparation of 4-(1,3,3-Trimethyl-7-oxabicyclo [4.1.0]hept-2-yl)but-3-en-2-one

To a 50-mL 2-neck reaction flask fitted with an addition funnel and an adapter connected to an apparatus similar to that described by Johnson and Schneider [*Org. Synth.*, 30, 18 (1950)] so that the mixture in the flask could be protected from atmospheric moisture, et al. throughout the course of the reaction were added a Teflon-coated spin bar, 1.254 g (5.81 mmoles) of 80% 3-chloroperoxybenzoic acid (purchased from Aldrich Chemical Co., Milwaukee, Wis.), and 10.0 mL of A.C.S. reagent-grade dichloromethane. After placing the flask in an ice-water bath (0° C.), a solution of 1.00 mL (4.84 mmoles) of alpha-ionone (purchased from Aldrich Chemical Co., Milwaukee, Wis.) in 5.0 mL of A.C.S. reagent-grade dichloromethane was added dropwise to the stirred reaction mixture over a period of 5 minutes. The resulting mixture was subsequently stirred at 0° C. for 2 hours. After dilution of the mixture with 40 mL of ether, the organic layer was washed twice with 50 mL portions of 4:1 (v/v) 1 M aqueous sodium hydroxide: 15% aqueous sodium chloride and once with 50 mL of saturated brine. The organic extracts were then dried over anhydrous sodium sulfate and subsequently filtered. Removal of the volatile organic solvents by evaporation at reduced pressure afforded 960 mg (95% yield) of the named epoxyketone. The identity and purity of this compound were ascertained by proton NMR analysis (recorded in $CDCl_3$ solution at 300 MHz). The latter spectrum exhibited a doublet of doublets (J=15.9, 10.2 Hz) at δ 6.73 (vinyl H), a doublet (J=15.9 Hz) at δ 6.103 (vinyl H adjacent to C=O), a singlet at δ 2.30 ($CH_3C$=O), a singlet at δ 1.260 ($CH_3$ bonded to C-1 in the bicyclic system), and singlets at δ 0.937 and 0.757 (two $CH_3$'s bonded to C-3 in the bicyclic system). For a previous synthesis of this named epoxide, see: D. W. Brooks, et al., *J. Org. Chem.*, 50, 628 (1985).

EXAMPLE II

Preparation of 4-(3-Hydroxy-2,6,6-trimethylcyclohex-1-enyl)-3-buten-2-one

To a 25-mL 1-neck reaction flask fitted with a reflux condenser connected to an apparatus similar to that described by Johnson and Schneider [*Org. Synth.*, 30, 18 (1950)] so that the mixture in the flask could be protected from atmospheric moisture, et al. throughout the course of the reaction were added 564 mg (2.71 mmoles) of epoxyketone produced in accordance with Example I, 3.0 mL of methyl alcohol (HPLC-grade, purchased from Aldrich Chemical Co., and 144 mg (1.04 mmoles) of anhydrous potassium carbonate. After sweeping the system briefly with nitrogen gas, the mixture was heated, with continuous stirring, at 65° C. (external oil bath temperature) for 3 hours. After cooling the mixture to room temperature, it was diluted with 30 mL of 1:1:1 (v/v/v) hexane:ether:dichloromethane and 20 mL of saturated brine mixed with 2 mL of 2 M aqueous HCl. After separating the layers, the organic layer was washed with 15% (w/v) aqueous sodium chloride (2×25 mL), then dried over anhydrous magnesium sulfate and filtered. Removal of the volatile organic solvents by evaporation at reduced pressure, followed by chromatography on Florisil [60 mL, 60–100 mesh, elution with 1:1 (v/v) hexane:ether] afforded 460 mg (82% yield) of the named hydroxy dienone. The identity and purity of this compound were ascertained by proton NMR analysis (recorded in $CDCl_3$ solution at 300 MHz). The latter spectrum exhibited a doublet (J=16.2 Hz) at $\delta$ 7.21 (C-4 vinyl H), a doublet (J=16.2 Hz) at $\delta$ 6.128 (C-3 vinyl H), a triplet (J=5 Hz) at $\delta$ 4.022 (CHOH), a singlet at $\delta$ 2.315 ($CH_3C=O$), and a singlet at $\delta$ 1.854 (vinyl $CH_3$). For previous syntheses of this named hydroxy dienone, see: T. Oishi, etal., *Tetrahedron Lett.*, 27, 203 (1986) and M. Rosenberger, et al., *J. Org. Chem.*, 47, 2130 (1982).

EXAMPLE III

Preparation of 3-(3-Hydroxy-3-methylpent-1-en-4-ynyl)-2,4,4-trimethylcyclohex-2-en-1-ol 12 mL of 0.5 M solution of ethynylmagnesium chloride (6 mmoles) in tetrahydrofuran (purchased from Aldrich Chemical Co., Milwaukee, Wis.) was added to a 100-mL 3-neck reaction flask fitted with an addition funnel and an adapter connected to an apparatus similar to that described by Johnson and Schneider [*Org. Synth.*, 30, 18 (1950)] so that the mixture in the flask could be protected from atmospheric moisture, et al. throughout the course of the reaction. After sweeping the system briefly with a stream of nitrogen gas and placing the flask in an ice-water bath (0° C.), a solution of 415 mg (1.99 mmoles) of hydroxy dienone (prepared as described in Example II) in 4.0 mL of anhydrous tetrahydrofuran was added dropwise over 5 minutes to the stirred Grignard reagent. The resulting mixture was stirred at 0° C. for an additional 90 minutes; after which it was diluted with 5 mL of hexane and the excess organometallic reagent was destroyed by slow, dropwise addition of 8 mL of saturated aqueous ammonium chloride. After allowing the mixture to warm to room temperature, it was diluted with 40 mL of 2:1:1 (v/v/v) ether:hexane:dichloromethane and 150 mL of saturated brine mixed with 5 mL of 2 M aqueous HCl. After separation from the aqueous layer, the organic layer was washed with saturated brine (2×120 mL), dried over anhydrous magnesium sulfate, and subsequently filtered. Removal of the volatile organic solvents by evaporation at reduced pressure afforded 450 mg (96.6% yield) of the named unsaturated diol. The identity and purity of this compound was ascertained by IR and proton NMR analysis (recorded in $CDCl_3$ solution at 300 MHz). The latter spectrum exhibited two doublets (J=16.2 Hz) at $\delta$ 6.386 and 5.598 (2 vinyl H's), a triplet (J=4.5 Hz) at $\delta$ 3.980 (CHOH), a singlet at $\delta$ 2.596 (C≡CH), a singlet at $\delta$ 1.798 (vinyl $CH_3$), a singlet at $\delta$ 1.613 ($CH_3$ adjacent to the tertiary alcohol functionality), and two singlets at $\delta$ 1.024 and 0.990 (two $CH_3$'s bonded to C-4).

EXAMPLE IV

Preparation of 3-(3-Hydroxy-3-methylpent-1-en-4-ynyl)-2,4,4-trimethylcyclohex-2-en-1-one To a 50-mL 1-neck reaction flask fitted with a reflux condenser connected to an apparatus similar to that described by Johnson and Schneider [*Org. Synth.*, 30, 18 (1950)] so that the mixture in the flask could be protected from atmospheric moisture, et al. throughout the course of the reaction were added 425 mg (1.81 mmoles) of unsaturated diol (prepared as described in Example III), 6.0 mL of acetone (HPLC-grade), 6.0 mL of dichloromethane (A.C.S. reagent-grade), and 844 mg (4.13 mmoles) of aluminum isopropoxide (purchased from Aldrich Chemical Co., Milwaukee, Wis.). After sweeping the system briefly with a stream of nitrogen gas, the mixture was heated at gentle reflux (40–45° C., external oil bath temperature) for 20 hours. After cooling the mixture to 0° C. (ice-$H_2O$ bath), 10 mL of 2 M aqueous HCl was added to hydrolyze any aluminum salts. This residual mixture was then diluted with 40 mL of saturated brine and 30 mL of 1:1:1 (v/v/v) ether:dichloromethane:hexane. After separating the layers, the organic layer was washed with 15% (w/v) aqueous sodium chloride (2×50 mL), dried over anhydrous magnesium sulfate, and subsequently filtered. Removal of the volatile organic solvents by evaporation at reduced pressure, subsequent addition of 5 mL of benzene to the residual material, and removal of the benzene accompanied by a small amount of isopropyl alcohol, afforded 410 mg (97.6% yield) of the named keto alkynol. The identity and purity of this compound were ascertained by IR and proton NMR analysis (recorded in $CDCl_3$ solution at 300 MHz). The latter spectrum exhibited two doublets (J=15.9 Hz) at $\delta$ 6.531 and 5.748 (2 vinyl H's), a singlet at $\delta$ 2.628 (C≡CH), a triplet (J=6.9 Hz) at $\delta$ 2.504 ($CH_2C=O$), a singlet at $\delta$ 1.80 (vinyl $CH_3$), a singlet at $\delta$ 1.643 ($CH_3COH$), and a singlet at $\delta$ 1.158 (two methyls bonded to C-4). The infrared spectrum exhibited the characteristic absorption peaks at $\nu$=3390 (OH), 3300 (C≡C—H), 1655 (C=O), and 1595 $cm^{-1}$ (C=C). For a previous synthesis of this named keto alkynol, see: European patent application 17,800 (Oct. 29, 1980)—which is cited in *Chem. Abstracts*, 94, 174463j (1981).

EXAMPLE V

Preparation of 3-(3-Oxobut-1-enyl)-2,4,4-trimethylcyclohex-2-en-1-one

To a 50-mL 2-neck reaction flask fitted with an additional funnel and a reflux condenser connected to an apparatus similar to that described by Johnson and Schneider [*Org. Synth.*, 30, 18 (1950)] so that the mixture in the flask could be protected from atmospheric moisture, et al. throughout the course of the reaction were added a Teflon-coated spin bar and 1.0 mL of dimethyl sulfoxide (HPLC-grade). After sweeping the system briefly with a stream of nitrogen gas, the flask was heated to a temperature of approximately 100° C. (external oil bath temperature: 100–102° C.). At that point, a solution of 3.81 g (17.7 mmoles) of pyridinium chlorochromate and 1.00 mL (4.91 mmoles) of beta-ionone (both of which reactants were purchased from Aldrich Chemical Co., Milwaukee, Wis.) in 7.0 mL of HPLC-grade dimethyl sulfoxide was added dropwise to the reaction flask over a period of 30 minutes. This mixture was subsequently stirred at 100° C. for 12 hours. After cooling the mixture to room temperature, it was diluted with 50 mL of 2:2:1 (v/v/v) ether:hexane:dichloromethane, 50 g of crushed ice, and 125 mL of ice-cold 1 M aqueous sodium hydroxide. After swirling this mixture for several minutes, it was diluted with 150 mL of 15% (w/v) aqueous sodium chloride and the layers were separated. The organic layer was subsequently washed in successive order with 100 mL of 1:1 (v/v) 1 M aqueous NaOH: 15% (w/v) aqueous NaCl, two times with 50 mL portions of 1:1 (v/v) 2 M aqueous HCl: 15% (w/v) aqueous NaCl, 50 mL of 15% (w/v) aqueous NaCl, and 50 mL of saturated brine. The washed organic layer was then dried over anhydrous magnesium sulfate and subsequently filtered. Removal of the volatile organic solvents by evaporation at reduced pressure afforded 618 mg (61% yield) of the named diketone. The identity and purity of this compound were ascertained by comparison of its IR and proton NMR spectral properties with those previously reported for the same structure by E. Becher, et al., *Helv. Chim. Acta,* 64, 2419 (1981). For a more economical route to convert beta-ionone to the named diketone (the common name of which is 4-oxo-beta-ionone), see: Japanese patent 81,161, 370 (Dec. 11, 1981), which is cited in *Chem. Abstracts,* 96, 199941t (1982).

EXAMPLE VI

An Alternate Route to 3-(3-Hydroxy-3-methylpent-1-en-4-ynyl)-2,4,4-trimethylcyclohex-2-en-1-one 10 mL of 0.5M solution of ethynylmagnesium chloride (5 mmoles) in tetrahydrofuran (purchased from Aldrich Chemical Co., Milwaukee, Wis.) was added to a 100 mL 3-neck reaction flask fitted with an addition funnel and an adapter connected to an apparatus similar to that described by Johnson and Schneider [*Org. Synth.,* 30, 18 (1950)] so that the mixture in the flask could be protected from atmospheric moisture, et al. throughout the course of the reaction. After sweeping the system briefly with a stream of nitrogen gas and placing the flask in an ice-water bath (0° C.), a solution of 600 mg (2.91 mmoles) of 4-oxo-beta-ionone (prepared as described in Example V) in 4.0 mL of anhydrous tetrahydrofuran was added rapidly to the stirred Grignard reagent. The resulting mixture was stirred at 0° C. for an additional 60 minutes; after which it was diluted with 5 mL of hexane and the excess organometallic reagent was destroyed by slow, dropwise addition of 6 mL of saturated aqueous ammonium chloride. Isolation of the product as described in the procedure of Example III afforded 703 mg of a mixture of products, the major component of which was shown by proton NMR analysis to be the named keto alkynol (characterized by a singlet at $\delta$ 1.158—ascribed to the two methyls bonded to C-4). The other product was shown to be a diyne-diol (i.e., the bis Grignard adduct obtained by addition of ethynylmagnesium chloride to both carbonyl groups in 4-oxo-beta-ionone). The systematic name of the latter by-product is 1-ethynyl-3-(3-hydroxy-3-methylpent-1-en-4-ynyl)-2,4,4-trimethylcyclohex-2-en-1-ol; and its proton NMR spectrum is characterized by a singlet at $\delta$ 1.02—ascribed to the two methyls bonded to C-4. Upon treatment with powdered NaOH in a non-polar organic solvent at room temperature, the latter diyne-diol was converted to the desired product, the named keto alkynol. As described by the following procedure, this transformation can be conducted without the need for separation of the above mixture of products.

To a 25-mL 1-neck reaction flask fitted with an adapter connected to an apparatus similar to that described by Johnson and Schneider [*Org. Synth.,* 30, 18 (1950)] so that the mixture in the flask could be protected from atmospheric moisture, et al. throughout the course of the reaction were added a Teflon-coated spin bar, 352 mg of the above product mixture, 6.0 nL of benzene (spectrophotometric-grade, purchased from Aldrich Chemical Co., Milwaukee, Wis.), and 125 mg of powdered NaOH. After sweeping the system briefly with a stream of nitrogen gas, the mixture was stirred vigorously at room temperature for 15 hours.

[NOTE: If the mixture is heated at a temperature of 78–80° C. (external oil bath temperature) after fitting the flask with a reflux condenser, the product obtained is 4-oxo-beta-ionone (not the desired keto alkynol), even after a reaction time of 40 minutes!] At that point, an additional 40 mg of powdered sodium hydroxide was added to the reaction mixture; and stirring was continued for an additional 6 hours at room temperature. The mixture was then diluted with 30 mL of 1:1:1 (v/v/v) ether:hexane:dichloromethane and 20 mL of 15% (w/v) aqueous sodium chloride. After separating the layers, the organic layer was washed with 15% (w/v) aqueous NaCl (2×15 mL), then dried over anhydrous magnesium sulfate and filtered. Removal of the volatile organic solvents by evaporation at reduced pressure and subsequent evaporative ("Kugelrohr oven") distillation in the presence of 5 mg of powdered $CaCO_3$ afforded 264 mg (78% overall yield, based on the starting diketone, 4-oxo-beta-ionone) of the named keto alkynol: boiling point 125–137° C. (bath temperature, 0.35 mm). The IR and proton NMR spectra of this material were identical to those exhibited by the product prepared in accordance with the procedure of Example IV.

NOTE: Use of powdered KOH in lieu of powdered NaOH in the experiment described above also yielded the desired keto alkynol. Other non-polar solvents (e.g., isopropyl ether) were used successfully in this experiment in lieu of benzene. However, use of polar organic solvents such as dimethyl sulfoxide (DMSO) is not recommended. When DMSO was used as the solvent, the starting material was rapidly consumed, but the product consisted of a mixture of unidentified compounds—different from the named keto alkynol and 4-oxo-beta-ionone.

EXAMPLE VII

Preparation of 2-[3-Methyl-5-(2,6,6-trimethyl-3-oxocyclohex-1-enyl)penta-1,2,4-trienyl]-1,3,2-dioxaphospholan-2-one To a 15-mL 2-neck reaction flask fitted with an adapter connected to an apparatus similar to that described by Johnson and Schneider [*Org. Synth.,* 30, 18 (1950)] so that the mixture in the flask could be protected from atmospheric moisture, et al., throughout the course of the reaction were added 90 mg (0.39 mmole) of distilled keto alkynol prepared as described in Example VI, 0.10 mL (0.72 mmole) of triethylamine (purchased from Aldrich Chemical Co., Milwaukee, Wis.), 1 mg of hydroquinone (or other suitable antioxidant), and 1.0 mL of A.C.S. reagent-grade dichloromethane. After placing the flask in an ice-water bath (0° C.), 50 microliters (0.56 mmole) of 2-chloro-1,3,2-dioxaphospholane (purchased from Aldrich Chemical Co.) was added dropwise via syringe while simultaneously maintaining the stirred reaction mixture under a gentle stream of nitrogen gas. The resulting mixture was stirred at 0° C. for an additional 10 minutes and subsequently at room temperature for 2 hours. After dilution of the mixture with 30 mL of 2:1 (v/v) hexane:dichloromethane the organic layer was washed in successive order with 20 mL portions of 10%

(w/v) aqueous NaCl and saturated brine. The organic layer was then dried over anhydrous magnesium sulfate and subsequently filtered. Removal of the volatile organic solvents by evaporation at reduced pressure, subsequent addition of 2 mL of benzene to the residual material, and removal of the benzene accompanied by trace amounts of triethylamine under reduced pressure afforded 109 mg (87% yield) of the named allenic phosphonate. The identity and purity of this compound were ascertained by IR (1935 cm$^{-1}$, C=C=C; 1660 cm$^{-1}$, C=O) and proton NMR analysis (recorded in CDCl$_3$ solution at 300 MHz). The latter spectrum exhibited a broad singlet at δ 5.62 (C-1 vinyl H), two multiplets at δ 4.48 and 4.23 (OCH$_2$CH$_2$O), a triplet (J=6.9 Hz) at δ 2.501 (CH$_2$C=O), a multiplet at δ 1.986 (CH$_3$ bonded to C-3), a singlet at δ 1.816 (vinyl methyl bonded to the ring), and a singlet at δ 1.17 (two methyls). Storage of this compound in the presence of a small amount of a suitable antioxidant (e.g., hydroquinone) is recommended.

EXAMPLE VIII

Preparation of 3-Methyl-5-(2,6,6-trimethyl-3-oxoycylohex-1-enyl)-1,2,4-pentatrienylphosphonic Acid, Diethyl Ester To a 15 mL 2-neck reaction flask fitted with an adapter connected to an apparatus similar to that described by Johnson and Schneider [*Org. Synth.*, 30, 18 (1950)] so that the mixture in the flask could be protected from atmospheric moisture, et al. throughout the course of the reaction were added 315 mg (1.36 mmoles) of keto alkynol prepared as described in Example IV, 0.35 mL (2.5 mmoles) of triethylamine (purchased from Aldrich Chemical Co., Milwaukee, Wis.), 2 mg of hydroquinone (or other suitable antioxidant), and 2.5 mL of dichloromethane (A.C.S. reagent-grade). After placing the flask in an ice-water bath (0° C.), 0.25 mL of diethyl chlorophosphite (95%, purchased from Aldrich Chemical Co.) was added dropwise via syringe while simultaneously maintaining the stirred reaction mixture under a gentle stream of nitrogen gas. The resulting mixture was stirred at 0° C. for an additional 10 minutes and subsequently at room temperature for 2.5 hours. The mixture was then cooled to approximately 0° C. by means of an external ice-H$_2$O bath, and 0.10 mL of water was added to destroy any unreacted diethyl chlorophosphite. After dilution of the mixture with 30 mL of 2:1 (v/v) hexane:dichloromethane, the organic layer was washed in successive order with 25 mL portions of 10% aqueous sodium chloride and saturated brine. The organic extracts were then dried over anhydrous magnesium sulfate and subsequently filtered. Removal of the volatile organic solvents by evaporation at reduced pressure, subsequent addition of 5 mL of benzene to the residual material, and removal of the benzene accompanied by trace amounts of triethylamine under reduced pressure afforded 458 mg (96% yield) of the named allenic phosphonate. The identity of this compound was ascertained by proton NMR analysis (recorded in CDCl$_3$ solution at 400 MHz). The latter spectrum exhibited a singlet at δ 6.172 (2 vinyl H's at C-4 and C-5), a multiplet at δ 5.546 (C-1 vinyl H), a multiplet at δ 4.121 (two OCH$_2$ moieties), a triplet (J=6.8 Hz) at δ 2.50 (CH$_2$C=O), a multiplet at δ 1.982 (CH$_3$ bonded to C-3), a singlet at δ 1.821 (vinyl CH$_3$ on the ring), a triplet (J=7 Hz) at δ 1.331 (2×CH$_3$ in the phosphonate moiety), and a singlet at δ 1.18 (2×CH$_3$ on the ring). It is recommended that this unsaturated phosphonate be stored in the presence of a small amount of a suitable antioxidant (e.g., hydroquinone).

NOTE: In lieu of purchasing diethyl chlorophosphite from Aldrich Chemical Co., it can be prepared from phosphorous trichloride and ethyl alcohol in accordance with a procedure suggested by J. Michalski, et al., *J. Chem. Soc.*, 4904 (1961).

EXAMPLE IX

Partial Reduction of 3-Methyl-5-(2,6,6-trimethyl-3-oxocyclohex-1-enyl)-1,2,4-pentatrienylphosphonic Acid, Diethyl Ester In accordance with a procedure suggested by B. C. Ranu, et al., *J. Org. Chem.*, 63, 5250 (1998), the following experiment was conducted: to a 25 mL 1-neck reaction flask fitted with a reflux condenser connected to an apparatus similar to that described by Johnson and Schneider [*Org. Synth.*, 30, 18 (1950)] so that the mixture in the flask could be protected from atmospheric moisture, et al. throughout the course of the reaction were added 246 mg (0.70 mmole) of allenic phosphonate produced in accordance with Example VIII, 2 mg of hydroquinone (or other suitable antioxidant), 6.0 mL of methyl alcohol (HPLC-grade, purchased from Aldrich Chemical Co.), 54 mg (0.86 mmole) of ammonium formate, and 42 mg of 10% Pd-C (purchased from Aldrich Chemical Co.). After sweeping the system briefly with nitrogen gas, the mixture was heated, with vigorous stirring, at 60–65° C. (external oil bath temperature) for 7 hours. After cooling the mixture to room temperature, the product was isolated by dilution of the reaction mixture with 50 mL of 4:1 (v/v) ether:dichloromethane and removal of the palladium catalyst by filtration through a small pad of Hytlo Super-Cel® filtering aid. The filtrate was subsequently washed with saturated brine (2×50 mL), then dried over anhydrous magnesium sulfate and filtered. Removal of the ether and dichloromethane by evaporation at reduced pressure afforded 186 mg (75% yield) of an unsaturated phosphonate identified as 3-methyl-5-(2,6,6-trimethyl-3-oxocyclohex-1-enyl)-2,4-pentadienylphosphonic acid, diethyl ester, by IR and proton NMR (recorded at 400 MHz) analysis. IR analysis of this unsaturated phosphonate indicated that the double bond between C-1 and C-2 had been reduced [i.e., lack of absorption at 1935 cm$^{-1}$ arising from the allenic moiety (C=C=C)]. The proton NMR spectrum exhibited two doublets (J=16 Hz) at δ 6.256 and 6.164 (2 vinyl H's at C-4 and C-5), a multiplet at δ 5.61 (C-2 vinyl H), a doublet of doublets (J=23.1, 8.1 Hz) at δ 2.761 (CH$_2$P), and a triplet (J=6.9 Hz) at δ 2.505 (CH$_2$C=O).

EXAMPLE X

Preparation of Canthaxanthin

To a solution of 150 mg (0.423 mmole) of 3-methyl-5-(2,6,6-trimethyl-3-oxocyclohex-1-enyl)-2,4-pentadienylphosphonic acid, diethyl ester (produced in accordance with Example IX) and 22 mg (0.13 mmole) of 2,7-dimethyl-2,4,6-octatrienedial (prepared as described in Example XIV of U.S. Pat. No. 5,061,819) in 1.10 mL of 10:1 (v/v) anhydrous tetrahydrofuran:dimethyl sulfoxide, protected from atmospheric moisture and maintained at a temperature of approximately 5° C. by use of an external ice-water bath was added 47 mg (0.42 mmole) of potassium tert-butoxide. This mixture was subsequently stirred in the cold for 15 minutes and at room temperature for 2 hours. The product was isolated by dilution of the mixture with 25 mL of chloroform and subsequent washing of the organic layer with 5% (w/v) aqueous sodium chloride (3×20 mL). The organic layer was then dried over anhydrous magnesium sulfate and filtered. Removal of the volatile organic solvents by evaporation at reduced pressure, followed by filtration through a small column of "Baker-analyzed" silica gel (8 mL, 40-140 mesh, elution with 50 mL of benzene-20% ethyl acetate) to remove any unreacted allylic phosphonate afforded 38 mg (52% yield) of canthaxanthin, the identity of which was confirmed by comparison of its proton NMR spectrum with that exhibited by an authentic sample of canthaxanthin (purchased from Fluka Chemical Corp., Ron Kon Koma, New York).

What is claimed is:

1. An allenic phosphonate compound of the formula:

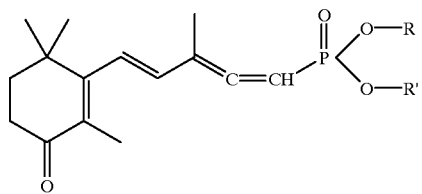

wherein R and R'=$C_1$–$C_4$ alkyl groups or R, R'=$(CH_2)_n$ (n=2 or 3).

2. The phosphonate of claim 1 which is:
3-methyl-5-(2,6,6-trimethyl-3-oxocyclohex-1-enyl)-1,2,4-pentatrienylphosphonic acid, diethyl ester.

3. The phosphonate of claim 1 which is:
3-methyl-5-(2,6,6-trimethyl-3-oxocyclohex-1-enyl)-1,2,4-pentatrienylphosphonic acid, dimethyl ester.

4. The phosphonate of claim 1 which is:
3-methyl-5-(2,6,6-trimethyl-3-oxocyclohex-1-enyl)-1,2,4-pentatrienylphosphonic acid, diisopropyl ester.

5. The phosphonate of claim 1 which is:
3-methyl-5-(2,6,6-trimethyl-3-oxocyclohex-1-enyl)-1,2,4-pentatrienylphosphonic acid, dipropyl ester.

6. The phosphonate of claim 1 which is:
3-methyl-5-(2,6,6-trimethyl-3-oxocyclohex-1-enyl)-1,2,4-pentatrienylphosphonic acid, dibutyl ester.

7. The phosphonate of claim 1 which is:
3-methyl-5-(2,6,6-trimethyl-3-oxocyclohex-1-enyl)-1,2,4-pentatrienylphosphonic acid, diisobutyl ester.

8. The phosphonate of claim 1 wherein R and R' form part of a 5- or 6-membered heterocyclic ring.

9. The phosphonate of claim 8 which is:
2-[3-methyl-5-(2,6,6-trimethyl-3-oxocyclohex-1-enyl) penta-1,2,4-trienyl]-1,3,2-dioxaphospholan-2-one.

10. An allylic phosphonate compound of the formula:

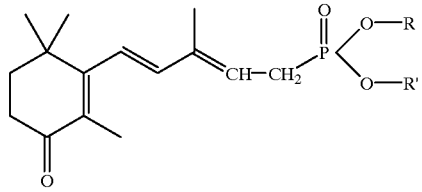

wherein R and R'=$C_1$–$C_4$ alkyl groups.

11. The phosphonate of claim 10 which is:
3-methyl-5-(2,6,6-trimethyl-3-oxocyclohex-1-enyl)-2,4-pentadienylphosphonic acid, diethyl ester.

12. The phosphonate of claim 10 which is:
3-methyl-5-(2,6,6-trimethyl-3-oxocyclohex-1-enyl)-2,4-pentadienylphosphonic acid, dimethyl ester.

13. The phosphonate of claim 10 which is:
3-methyl-5-(2,6,6-trimethyl-3-oxocyclohex-1-enyl)-2,4-pentadienylphosphonic acid, diisopropyl ester.

14. The phosphonate of claim 10 which is:
3-methyl-5-(2,6,6-trimethyl-3-oxocyclohex-1-enyl)-2,4-pentadienylphosphonic acid, dipropyl ester.

15. The phosphonate of claim 10 which is:
3-methyl-5-(2,6,6-trimethyl-3-oxocyclohex-1-enyl)-2,4-pentadienylphosphonic acid, dibutyl ester.

16. The phosphonate of claim 10 which is:
3-methyl-5-(2,6,6-trimethyl-3-oxocyclohex-1-enyl)-2,4-pentadienylphosponic acid, diisobutyl ester.

17. A method of preparing a C-15 allylic phosphonate compound of the formula:

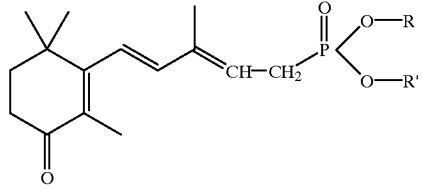

wherein R and R'=$C_1$–$C_4$ alkyl groups comprising the steps:

(I) forming a reaction mixture in a polar organic solvent comprising:

(a) an allenic phosphonate of the formula:

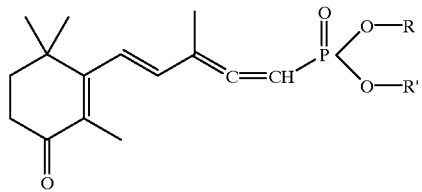

wherein R and R'=$C_1$–$C_4$ alkyl groups or R, R'=$(CH_2)_n$(n=2 or 3)

(b) ammonium formate or a trialkylammonium formate; and (c) a transition metal catalyst; and (II) maintaining the reaction mixture until the allylic phosphonate compound is formed.

18. The method of claim 17 wherein the organic solvent is an alcohol.

19. The method of claim 18 wherein the alcohol is selected from methanol, ethanol, and isopropyl alcohol.

20. The method of claim 17 wherein the reaction mixture includes one molar equivalent of ammonium formate.

21. The method of claim 17 wherein the transition metal catalyst is a palladium catalyst.

22. The method of claim 17 further comprising a step of stirring the reaction mixture while heating the reaction mixture to a temperature in excess of room temperature.

23. The method of claim 22 wherein the reaction mixture is heated to a temperature between about 50° C. and about 100° C.

24. A method of preparing canthaxanthin comprising the steps:

(I) reacting 3-(3-hydroxy-3-methylpent-1-en-4-ynyl)-2,4,4-trimethylcyclohex-2-en-1-one with diethyl chlorophosphite to form 3-methyl-5-(2,6,6-trimethyl-3-oxocyclohex-1-enyl)-1,2,4-pentatrienylphosphonic acid, diethyl ester;

(II) reacting the 3-methyl-5-(2,6,6-trimethyl-3-oxocyclohex-1-enyl)-1,2,4-pentatrienylphosphonic acid, diethyl ester with ammonium formate or a trialkylammonium formate to form 3-methyl-5-(2,6,6-trimethyl-3-oxocyclohex-1-enyl)-2,4-pentadienylphosphonic acid, diethyl ester; and (III) reacting the 3-methyl-5-(2,6,6-trimethyl-3-oxocyclohex-1-enyl)-2,4-pentadienylphosphonic acid, diethyl ester with 2,7-dimethyl-2,4,6-octatrienedial.

25. The method of claim 24 wherein about 1 equivalent of diethyl chlorophosphite is reacted with the 3-(3-hydroxy-3-methylpent-1-en-4-ynyl)-2,4,4-trimethylcyclohex-2-en-1-one in step (I).

26. The method of claim 24 wherein about one molar equivalent of ammonium formate is reacted with the 3-methyl-5-(2,6,6-trimethyl-3-oxocyclohex-1-enyl)-1,2,4-pentatrienylphosphonic acid, diethyl ester in step (II).

27. The method of claim 24 wherein the reaction of step (II) is carried out in the presence of a palladium catalyst.

28. The method of claim 24 wherein the reaction of step (II) is carried out in a polar organic solvent.

29. The method of claim 28 wherein the solvent is selected from methanol, ethanol, and isopropyl alcohol.

* * * * *

UNITED STATES PATENT AND TRADEMARK OFFICE
CERTIFICATE OF CORRECTION

PATENT NO. : 5,952,519

DATED : September 14, 1999

INVENTOR(S) : James H. Babler

It is certified that error appears in the above-identified patent and that said Letters Patent is hereby corrected as shown below:

At column 18, line 12, please delete "pentadienylphosponic" and insert - - pentadienylphosphonic - - therefor.

Signed and Sealed this

Thirtieth Day of May, 2000

Attest:

Q. TODD DICKINSON

*Attesting Officer*     *Director of Patents and Trademarks*